(12) United States Patent
Paterson et al.

(10) Patent No.: US 8,337,861 B2
(45) Date of Patent: Dec. 25, 2012

(54) COMPOSITIONS, METHODS AND KITS FOR ENHANCING THE IMMUNOGENICITY OF A BACTERIAL VACCINE VECTOR

(75) Inventors: Yvonne Paterson, Philadelphia, PA (US); Christian Peters, Radnor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 724 days.

(21) Appl. No.: 10/541,614

(22) PCT Filed: Jan. 8, 2004

(86) PCT No.: PCT/US2004/000366
§ 371 (c)(1),
(2), (4) Date: Apr. 27, 2006

(87) PCT Pub. No.: WO2004/062597
PCT Pub. Date: Jul. 29, 2004

(65) Prior Publication Data
US 2006/0233835 A1    Oct. 19, 2006

Related U.S. Application Data

(60) Provisional application No. 60/439,009, filed on Jan. 9, 2003.

(51) Int. Cl.
*A61K 39/02* (2006.01)
*A61K 48/00* (2006.01)

(52) U.S. Cl. .................. 424/234.1; 435/70.21

(58) Field of Classification Search .................. None
See application file for complete search history.

(56) References Cited

U.S. PATENT DOCUMENTS

| | | | | |
|---|---|---|---|---|
| 3,328,252 A | * | 6/1967 | Mora | 424/255.1 |
| 3,674,860 A | * | 7/1972 | Welter et al. | 424/269.1 |
| 4,160,452 A | | 7/1979 | Theeuwes | |
| 4,256,108 A | | 3/1981 | Theeuwes | |
| 4,265,874 A | | 5/1981 | Bonsen et al. | |
| 4,328,209 A | * | 5/1982 | Finkelstein et al. | 424/261.1 |
| 4,472,378 A | * | 9/1984 | Shuster et al. | 424/258.1 |
| 4,770,875 A | * | 9/1988 | Kume et al. | 424/253.1 |
| 5,010,062 A | * | 4/1991 | Hellergvist | 514/54 |
| 5,294,441 A | * | 3/1994 | Curtiss, III | 424/200.1 |
| 5,387,744 A | * | 2/1995 | Curtiss et al. | 424/258.1 |
| 5,436,001 A | * | 7/1995 | Kramer | 424/93.4 |
| 5,628,994 A | * | 5/1997 | Kaper et al. | 424/93.2 |
| 5,656,488 A | * | 8/1997 | Curtiss et al. | 435/252.33 |

(Continued)

FOREIGN PATENT DOCUMENTS

WO        01/25399    *    4/2001

(Continued)

OTHER PUBLICATIONS

Mankoski et al (1999), reference cited on US 1449.*

(Continued)

*Primary Examiner* — Albert Navarro
*Assistant Examiner* — Ginny Portner
(74) *Attorney, Agent, or Firm* — Mark S. Cohen; Pearl Cohen Zedek Latzer, LLP

(57) ABSTRACT

The present invention comprises methods for enhancing the immunogenicity of a bacterial vaccine vector and an antigen by passaging the bacterial vaccine vector through an animal.

12 Claims, 3 Drawing Sheets

U.S. PATENT DOCUMENTS

| | | | | |
|---|---|---|---|---|
| 5,783,386 | A * | 7/1998 | Jacobs et al. | 435/6 |
| 5,830,702 | A * | 11/1998 | Portnoy et al. | 435/69.3 |
| 5,855,879 | A * | 1/1999 | Curtiss, III | 424/93.2 |
| 5,855,880 | A * | 1/1999 | Curtiss et al. | 424/93.2 |
| 5,861,163 | A * | 1/1999 | Kim et al. | 424/260.1 |
| 5,869,091 | A * | 2/1999 | Carter et al. | 424/450 |
| 6,030,835 | A * | 2/2000 | Musser et al. | 435/340 |
| 6,051,237 | A * | 4/2000 | Paterson | 424/200.1 |
| 6,099,848 | A * | 8/2000 | Frankel et al. | 424/246.1 |
| 6,150,170 | A * | 11/2000 | Powell et al. | 435/455 |
| 6,190,657 | B1 * | 2/2001 | Pawelek et al. | 424/93.1 |
| 6,479,051 | B1 * | 11/2002 | Bruce et al. | 424/93.45 |
| 6,503,747 | B2 * | 1/2003 | Kathariou et al. | 435/252.3 |
| 6,565,852 | B1 * | 5/2003 | Paterson | 424/200.1 |
| 6,589,771 | B1 * | 7/2003 | Marshall | 435/243 |
| 6,733,761 | B2 * | 5/2004 | McKinney et al. | 424/248.1 |
| 6,767,542 | B2 * | 7/2004 | Paterson et al. | 424/192.1 |
| 6,855,320 | B2 * | 2/2005 | Paterson | 424/192.1 |
| 6,923,957 | B2 * | 8/2005 | Lowery et al. | 424/93.1 |
| 7,135,188 | B2 * | 11/2006 | Paterson | 424/277.1 |
| 7,314,624 | B2 * | 1/2008 | Baker et al. | 424/192.1 |
| 7,384,640 | B1 * | 6/2008 | Holmes et al. | 424/201.1 |
| 7,855,064 | B2 * | 12/2010 | Paterson et al. | 435/252.3 |
| 7,858,097 | B2 * | 12/2010 | Paterson et al. | 424/200.1 |
| 2001/0055759 | A1 * | 12/2001 | Kathariou et al. | 435/6 |
| 2002/0044926 | A1 * | 4/2002 | Reid et al. | 424/93.45 |
| 2002/0137215 | A1 * | 9/2002 | Francis et al. | 435/473 |
| 2002/0151031 | A1 * | 10/2002 | McKinney et al. | 435/232 |
| 2002/0177569 | A1 | 11/2002 | Kaufmann et al. | |
| 2002/0187162 | A1 * | 12/2002 | Geary et al. | 424/200.1 |
| 2003/0235577 | A1 * | 12/2003 | Shapiro et al. | 424/94.65 |
| 2004/0106553 | A1 * | 6/2004 | Alekshun et al. | 514/12 |
| 2004/0137003 | A1 * | 7/2004 | Curtiss, III | 424/184.1 |
| 2004/0219159 | A1 * | 11/2004 | Stewart et al. | 424/184.1 |
| 2005/0058663 | A1 * | 3/2005 | Monif | 424/200.1 |
| 2005/0180963 | A1 * | 8/2005 | Adams et al. | 424/93.45 |
| 2006/0233829 | A1 * | 10/2006 | Curtiss, III | 424/200.1 |
| 2007/0020237 | A1 * | 1/2007 | Yoon et al. | 424/93.2 |
| 2007/0128178 | A1 * | 6/2007 | Corthesy-Theulaz et al. | 424/93.45 |
| 2008/0102085 | A1 * | 5/2008 | Ertl et al. | 424/208.1 |
| 2009/0081250 | A1 * | 3/2009 | Paterson et al. | 424/200.1 |
| 2009/0186051 | A1 * | 7/2009 | Paterson et al. | 424/234.1 |
| 2009/0202587 | A1 * | 8/2009 | Paterson et al. | 424/200.1 |
| 2010/0291140 | A1 * | 11/2010 | Paterson et al. | 424/200.1 |

FOREIGN PATENT DOCUMENTS

WO    WO 01/25399    4/2001

OTHER PUBLICATIONS

Kleanthous et al, 2001 (reference icted on US 1449).*
Coulson, NM e al, Vaccine, 1994, Nov. vol. 12(15), pp. 1395-1401, *Bacillus anthracis* protective antigen, expressed in *Salmonella typhimurium* SL3261, affords protection against anthrax spore challenge.*
Friedlos, Frank et al, Clinical Cancer Research, 2008, vol. 14(13), Jul. 1, 2008, Attenuated *Salmonella* targets Prodrug activating enzyme carboxypeptidase G2 to mouse melanonma and human breat and colon carcinomas for Effective Suicide gene therapy.*
Roger D. Baker, Department of Pathology, Duke University School of Medicine, Durham, North Carolina, The Effect of mouse passage on cultural characteristics and virulence for mice of organisms causing blastomycosis, 1939, pp. 547-563 (photos).*
Vahidy, R. et al, Annals of the Academy of Medicine, Singapore, Jan. 1996, vol. 25(1), pp. 139-142, A comparative study of unpassaged and animal passaged cultures of *Listeria monocytogenes* in rabbits.*
Mackaness, G.B, 1962, Journal of Experimental Medicine, pp. 381-406, Sep. 1, 1962, vol. 116, Cellular Resistence to infection.*
Rayevskaya, M et al, Journal of Virology, Jan. 2002, pp. 918-922, vol. 76(2), Safety and Immunogenicity in Neonatal Mice of a Hyper attenuated *Listeria* vaccine Directed against Human Immunodeficiency Virus.*
Lemes-Marques et al, FEMS Microbiology Letters, 2004, pp. 63-70, vol. 239, Influence of environmental conditions on the expression of virulence factors by *Listeria monocytogenes* and their use in species identification.*
Szalay, G et al, PNAS vol. 92, pp. 12389-12392, Dec. 1995, Stimulation of protective CD8+ T lymphocytes by vaccination with non-living bacteria, teach "organisms were kept virulent by mouse passage".*
Shen, H et al, Cell, vol. 92, pp. 535-545, Feb. 20, 1998, Compartmentalization of Bacterial atnigens: Differential effects on priming of CD8 T-cells and Protective Immunity.*
Shata, Mohamed T et al, Molecular Medicine Today, Feb. 2000, vol. 6, pp. 66-71, Recent advances with recombinant bacterial vaccine vectors.*
von Koenig, Carl Heinz Wirsing et al, Infection and Immunity, vol. 40(3), pp. 1170-1177, Jun. 1983, Course of Infection and Development of Immunity in Experimental Infection of Mice with *Listeria serotypes.**
Mitsuyama, Maso et al, Medical Microbiology and Immunology, 1988, vol. 177, pp. 207-212, Generation of *Listeria monocytogenes* specific T-cells mediating delayed footpad reaction and protectin in neonatally thymectomized mice but not in nude mice.*
Berche et al. (1988) "Invasiveness and intracellular growth of *Listeria monocytogenes*." Infection 16:145-148.
Foley et al. (2001) "*Candidatus Mycoplasma haemominutum*, a low virulence epierythrocytic parasite of cats" International Journal of Systematic and Evolutionary Microbiology, 51(3):815-817.
Goossens et al. (1995), "Attenuated *Listeria monocytogenes* as a live vector for induction of CD8+ T cells in vivo: a study with the nucleoprotein of the lymphocytic choriomeningitis virus." Int. Immunol. 7:797-802.
Gunn et al.(2001) "Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16." J. Immunol. 167:6471-6479.
Harris et al. (1986) "Molecular basis for heterogeneity of the human p53 protein." Mol. Cell. Biol. 6:4650-4656.
Ikonomidis et al. (1997) "Influenza-specific immunity induced by recombinant *Listeria monocytogenes* vaccines." Vaccine 15:433-440.
Kaufmann (1993) "Immunity to intracellular bacteria" Ann. Rev. Immunol. 11:129-163.
Kleanthous, H et al. (2001) "Sterilizing immunity against experimental *Helicobater pylori* infection is challenge-strain dependent." Vaccine 14, 19(32):4883-4895.
Mankoski et al. (1999) "flaA mRNA transcription level correlates with *Helicobactor pyloricolonisation* efficiency in gnotobiotic piglets." Journal of Medical Microbiology, 48(4):395-399.
Mata et al. (2001) "Evaluation of a recombinant *Listeria monocytogenes* expressing an HIV protein that protects mice against viral challenge." Vaccine 19:1435-1445.
Merino et al. (2002) "A hypermutator phenotype a attenuates the virulence of *Listeria monocytogens* in a mouse model." Molecular Microbiology, 44(3):877-887.
Pan et al. (1995), "A recombinant *Listeria monocytogenes* vaccine expressing a model tumour antigen protects mice against lethal tumour cell challenge and causes regression of established tumours." Nat. Med. 1:471-477.
Paterson et al. (1996) "Recombinant *Listeria monocytogenes* cancer vaccines." Curr. Opin. Immunol. 8:664-669.
Shen et al. (1995) "Recombinant *Listeria monocytogenes* as a live vaccine vehicle for the induction of protective anti-viral cell-mediated immunity." Proc. Natl. Acad. Sci. USA 92:3987-3991.
Vahidy et al. (1996) "A comparative study of unpassaged and animal passaged cultures of *Listeria monocytogenes* in rabbits." Ann Acad Med. Singapore 25:139-553.
Peters et al., "Enhancing the immunogenicity of bioengineered *Listeria monocytogenes* by passaging through live animal hosts", Vaccine, vol. 21, Issues 11-12, pp. 1187-1194 , 2003.
Weiskirch et al., "*Listeria monocytogenes*: a potent vaccine vector for neoplastic and infectious diseases", Immunol. Reviews, 1997, vol. 158, pp. 159-169.

* cited by examiner

SEQUENCE LISTING

```
<160> NUMBER OF SEQ ID NOS: 3

<210> SEQ ID NO 1
<211> LENGTH: 9
<212> TYPE: PRT
<213> ORGANISM: Human immunodeficiency virus

<400> SEQUENCE: 1

Ala Met Gln Met Leu Lys Glu Thr Ile
1               5

<210> SEQ ID NO 2
<211> LENGTH: 9
<212> TYPE: PRT
<213> ORGANISM: Listeria monocytogenes

<400> SEQUENCE: 2

Gly Tyr Lys Asp Gly Asn Glu Tyr Ile
1               5

<210> SEQ ID NO 3
<211> LENGTH: 9
<212> TYPE: PRT
<213> ORGANISM: Human papillomavirus

<400> SEQUENCE: 3

Arg Ala His Tyr Asn Ile Val Thr Phe
1               5
```

COMPOSITIONS, METHODS AND KITS FOR ENHANCING THE IMMUNOGENICITY OF A BACTERIAL VACCINE VECTOR

CROSS-REFERENCE TO RELATED APPLICATIONS

This application is a National Phase Application of PCT International Application No. PCT/US2004/000366, International Filing Date Jan. 8, 2004, claiming priority of U.S. Provisional Patent Application No. 60/439,009, filed Jan. 9, 2003.

BACKGROUND OF THE INVENTION

Vaccines represent the most beneficial and cost effective public health measure currently known. However, as the understanding of neoplasias and infectious diseases grows, it has become apparent that traditional vaccine strategies may not be completely effective. Traditional vaccines have employed killed or attenuated organisms or antigen subunits in order to elicit immunity in an animal. There are some limitations to these approaches especially in the case of killed or subunit vaccines, in that the immune response in the vaccinated animal is primarily humoral in nature and therefore is not effective in combating intracellular organisms or tumors that require cell mediated immunity for their destruction.

The first vaccination campaign is widely attributed to Edward Jenner, who used cowpox to immunize dairymaids against the ravages of small pox. This was closely followed by Louis Pasteur's use of live, attenuated bacteria in the 19th century. As a result, vaccines effective against *Mycobacterium tuberculosis, Salmonella typhi, Vibrio cholerae* and *Bordetella pertussis* exist. Unfortunately, attenuated or inactivated bacteria often only induce immunization for a short period of time and immunity is limited to a humoral response. Further, traditional attenuated or inactivated bacterial vaccines do not elicit the cytotoxic T-lymphocyte (CTL) immune response necessary for the lysis of tumor cells and cells infected with intracellular pathogens.

Viral vaccines are often used to induce a CTL response in a vaccinee. Viral vaccines are usually pathogenic viruses attenuated by serial passage in cell culture or viruses killed through heat or chemical inactivation. Killed viruses are incapable of infecting cells, and thus, like subunit vaccines, primarily elicit a humoral immune response. Attenuated viruses are capable of infecting cells, and can induce a CTL response in an individual. However, attenuated virus vaccines are not without drawbacks. First, attenuating a virus is often a process of trial and error. For example, the yellow fever vaccine strain was developed only after more than 200 passages in cell culture, after which a spontaneous mutation resulted in the attenuated phenotype. Second, there is a serious safety issue in using attenuated viruses, especially in children, the elderly, and the immunocompromised.

A solution to the problems of traditional bacterial and viral vaccines exists in DNA vaccines and bacterial vaccine vectors such as *Salmonella* and *Listeria* species. DNA vaccines are usually plasmids comprising a nucleic acid encoding an antigen, and elicit to a strong humoral and cell-mediated immune response because the antigen is translated in the transfected cell, facilitating an MHC-mediated cellular response, and expressed in the extracellular milieu, enabling a humoral response. Moreover, DNA vaccines can express an incredibly wide repertoire of proteins, including antigens, cytokines, and enzymes.

*Listeria monocytogenes* (*L. monocytogenes*) vaccine vectors are equally adept at expressing a wide array of heterologous antigens and inducing a CTL response, as demonstrated by Portnoy and Paterson (U.S. Pat. No. 5,830,702). *L. monocytogenes* is a beta hemolytic gram positive facultative intracellular microbe. Further, *L. monocytogenes* is the prototypic intracellular bacterial pathogen which elicits a predominantly cellular immune response when inoculated into an animal (Kaufmann, 1993, Ann. Rev. Immunol. 11:129-163). Upon infection of a cell, *Listeria* escape the lysosome by disrupting the phagosomal membrane through the action of listeriolysin O (LLO), a hemolytic enzyme. *Listeria* then replicate in the cytoplasm of the infected cell, and therefore, humoral immunity is virtually useless in controlling the pathogenesis of *Listeria*. However, *L. monocytogenes* peptides are presented through both the MHC class I and class II pathways, and therefore cellular immunity is stimulated by *L. monocytogenes* infection. These properties have peaked interest in *L. monocytogenes* as a vaccine vector. When used as a vector for the transmission of genes encoding heterologous antigens derived from infectious agents or from tumor cells, recombinant *Listeria* expressing an appropriate heterologous antigen have been shown to successfully protect mice against challenge by lymphocytic choriomeningitis virus (Shen et al., 1995, Proc. Natl. Acad. Sci. USA 92:3987-3991; Goossens et al., 1995, Int. Immunol. 7:797-802) and influenza virus (Ikonomidis et al., 1997, Vaccine 15:433-440). Further, heterologous antigen expressing recombinant *Listeria* have been used to protect mice against lethal tumor cell challenge (Pan et al., 1995, Nat. Med. 1:471-477; Paterson and Ikonomidis, 1996, Curr. Opin. Immunol. 8:664-669).

With the advent of *Listeria* vaccines, and bacterial vaccine vectors in general, a new problem has arisen. The effectiveness of *Listeria* (or, indeed, any live, attenuated bacteria) as a vaccine vector depends on its ability to induce strong, long-lived immune responses to the passenger antigen. Bioengineering techniques tend to decrease the virulence of *Listeria*, probably because the expression of virulence factors needed for in vivo survival in the host is either abrogated or reduced. Avirulent bacteria do not, as a rule, invoke strong immune responses. Thus, although bioengineering techniques make it possible to use *Listeria* as a vaccine vector, they also decrease its efficacy significantly.

The process of introducing a new gene to the bacterial genome requires extensive propagation of the bacterium in a rich medium optimized for bacterial growth in vitro. In such media, bacteria do not need to express the virulence factors that they would need to survive the hostile environment of a host during infection. Indeed, cultivated bacteria may shut down virulence factors not needed in an in vitro growth medium. For example, the expression of the essential virulence factor LLO (required for the escape of *Listeria* from the phagolysosome) is shut down in iron-rich medium (Berche et al, 1988, Infection 16:145-148). When in vitro cultured bacteria are subjected to in vivo conditions, the bacteria are not able to reactivate their virulence factors rapidly enough to avoid the host's innate immune defenses. Thus a bacterial vaccine vector based on *Listeria* may fail to be efficacious. A method to restore and enhance the virulence of bacteria for experimental purposes is to passage the organisms through animals (Vahidy et al, 1996, Ann Acad Med. Singapore 25:139-553). The molecular basis for this method is not known, but it is thought that passaged bacteria are able to more effectively and rapidly regulate their virulence factors.

Given the demonstrated uses of *Listeria* as a vaccine vector, there exists a long felt need for methods to construct

*Listeria* vaccine vectors capable of eliciting a strong immune response. The present invention meets this need.

BRIEF SUMMARY OF THE INVENTION

In one aspect, the present invention comprises a method of enhancing the immunogenicity of a bacterial vaccine vector. The method comprises administering to an animal the bacterial vaccine vector, passaging the bacterial vaccine vector through the animal, harvesting the bacterial vaccine vector from the animal, and repeating these steps until a maximum bacterial load in an organ is reached, thereby enhancing the immunogenicity of the *Listeria* vaccine vector.

In another aspect, the organ is a spleen or liver.

In another aspect, the bacterial vaccine vector expresses an antigen.

In yet another aspect, the antigen is a heterologous antigen.

In still another aspect, the antigen is a tumor antigen.

In one aspect of the invention, the bacterial vaccine vector is a *Listeria* vaccine vector.

In another aspect of the invention, the animal is a mammal.

In another aspect, the mammal is a mouse.

In one aspect of the present invention, the bacterial vaccine vector is administered to the animal via oral or parenteral administration.

The present invention further comprises a bacterial vaccine vector having enhanced immunogenicity wherein the immunogenicity of the bacterial vaccine vector is enhanced by administering to an animal the bacterial vaccine vector, passaging the bacterial vaccine vector through the animal, harvesting the bacterial vaccine vector from the animal, and repeating these steps until a maximum bacterial load in an organ is reached.

In one aspect, the organ is a spleen or liver.

In another aspect, the bacterial vaccine vector expresses an antigen.

In still another aspect, the antigen is a heterologous antigen.

In yet another aspect, the antigen is a tumor antigen.

In one aspect of the present invention, the bacterial vaccine vector is a *Listeria* vaccine vector.

In another aspect, the animal is a mammal.

In another aspect, the mammal is a mouse.

In one aspect, the bacterial vaccine vector is administered to the animal via oral or parenteral administration.

In still another aspect, the bacterial vaccine vector comprises a pharmaceutically acceptable carrier.

The present invention includes a method of enhancing the immunogenicity of an antigen expressed from a bacterial vaccine vector. The method comprises administering to an animal the bacterial vaccine vector, passaging the bacterial vaccine vector through the animal harvesting the bacterial vaccine vector from the animal, and repeating these steps until a maximum bacterial load in an organ is reached, thereby enhancing the immunogenicity of the antigen expressed from a bacterial vaccine vector.

In one aspect, the organ is a spleen or liver.

In another aspect, the antigen is a heterologous antigen.

In yet another aspect, the antigen is a tumor antigen.

In still another aspect, the bacterial vaccine vector is a *Listeria* vaccine vector.

In one aspect of the present invention, the animal is a mammal.

In another aspect, the mammal is a mouse.

In another aspect, the bacterial vaccine vector is administered to the animal via oral or parenteral administration.

The present invention further comprises a kit comprising a bacterial vaccine vector having enhanced immunogenicity, wherein the kit comprises an applicator and an instructional material for use thereof.

In one aspect, the bacterial vaccine vector is lyophilized.

In another aspect, the kit further comprises a pharmaceutically acceptable carrier.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A depicts the effect of passaging on Lm-Gag. FIG. 1B depicts the effect of passaging on Lm-LLO-E7. The average colony forming units (CFU) of live bacteria per milliliter in spleen homogenate from four mice is shown.

FIG. 3, comprising FIGS. 3A, 3B, 3E and 3F and FIGS. 3C, 3D, 3G and 3H depict antigen-specific T-cells from mice immunized with $10^3$ CFU or $10^5$ CFU passaged *Listeria* vaccine vectors, respectively. FIGS. 3B, 3D, 3F, 3H depict antigen-specific T-cells from mice immunized with unpassaged *Listeria* vaccine vectors. FIGS. 3A through 3D depict the immune response to MHC class I HIV-Gag peptide and FIGS. 3E-3H depict the immune response to an LLO peptide. FIG. 3I depicts splenocytes from mice immunized with $10^5$ CFU passaged Lm-Gag stimulated with a control peptide from human papilloma virus (HPV) E7.

DETAILED DESCRIPTION OF THE INVENTION

Figure 1A:
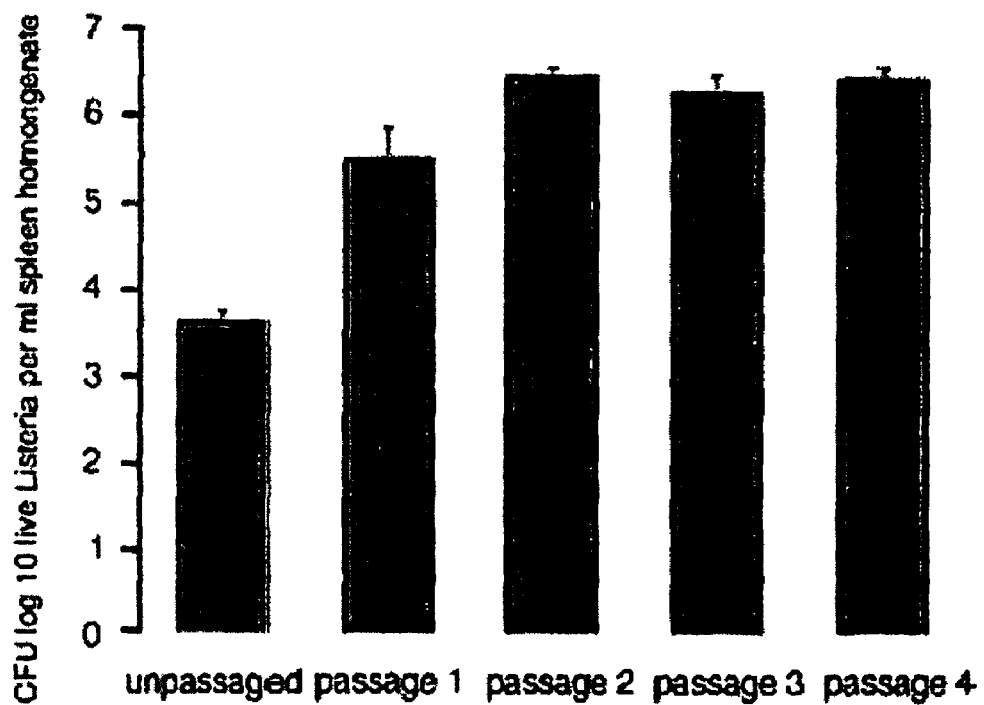
FIG. 1A and FIG. 1B, is a series of graphs depicting the effect of passaging on bacterial load (virulence) of recombinant *Listeria* vaccine vectors.

Bacterial vaccine vectors, such as *Listeria monocytogenes* vaccine vectors are capable of expressing heterologous antigens and also inducing a cytotoxic T-lymphocyte (CTL) response in a vaccinated individual, and therefore represent great promise in the prevention of tumors and infectious diseases. The data disclosed herein demonstrate, for the first time, a method for enhancing the immunogenicity of a bacterial vaccine vector and the antigen expressed by the bacterial vaccine vector, thereby increasing its potency as a vaccine.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Antigen" is used herein to refer to a substance that when placed in contact with an organism, results in a detectable immune response. An antigen may be a lipid, peptide, protein, carbohydrate, nucleic acid, or combinations and variations thereof.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

"Harvesting" or "harvested" is used herein to refer to the process of recovering an organism, such as a bacteria, from an animal after it has been administered to the animal. Harvesting can comprise, among other things, drawing blood or other bodily fluids such as lymph, urine, or sputum, and/or removing a cell, a tissue and/or an organ, wherein the body fluid, tissue and/or organ comprises the organism administered to the animal.

"Heterologous antigen" is used herein to refer to an antigen that is not endogenous to the organism comprising or expressing an antigen. As an example, a bacterial vaccine vector comprising or expressing a viral or tumor antigen comprises a heterologous antigen.

"Immunogenicity" is used herein to refer to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to the animal. The increased ability of an antigen or organism to elicit an immune response can be measured by, among other things, a greater number of antibodies that bind to an antigen or organism, a greater diversity of antibodies to an antigen or organism, a greater number of T-cells specific for an antigen or organism, a greater cytotoxic or helper T-cell response to an antigen or organism, a greater expression of cytokines in response to an antigen, and the like.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"*Listeria* mutant" is used herein to refer to a *Listeria* bacteria where a gene has been modified, altered, removed, or otherwise inactivated such that the gene does not encode a protein that is present in a wild-type *Listeria* bacteria.

"*Listeria* vaccine vector" is used herein to refer to a *Listeria* bacteria that expresses a heterologous, endogenous, or fusion protein antigen when administered to an animal.

"Maximum bacterial load" is used herein to refer to the greatest number of bacteria harvested from an animal after one or more passages of the bacteria through the animal. The maximum bacterial load is measured in comparison to the number of bacteria harvested from the previous passage and the number of bacteria harvested from the following passage. Thus, if the number of bacteria harvested from the previous passage is less than the number of bacteria harvested from the present passage, and the number of bacteria harvested from the following passage is less than the number of bacteria harvested from the present passage, the present passage represents the maximum bacterial load.

"Maximum bacterial virulence" is used herein to refer to a state in which bacteria grow or replicate at a detectably greater rate, either in vivo or in vitro, than bacteria that were not passaged through an animal.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Passaging" is used herein to refer to the process of administering an organism, such as a bacteria, to an animal, allowing the organism to grow and/or replicate in the animal, and then collecting the organism from the animal, thereby passing the organism through the animal.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Tumor antigen" is used herein to refer to an antigen that is expressed on a tumor, or is used to identify or diagnose a tumor in a mammal.

"Transform", "transforming", and "transformation" is used herein to refer to a process of introducing an isolated nucleic acid into the interior of an organism.

As disclosed elsewhere herein, while *Listeria* is an excellent vaccine vector, the genetic manipulation and in vitro cultivation necessary to develop an effective vaccine vector may diminish the immunogenicity of *Listeria* to a degree that the *Listeria* based bacterial vaccine vector becomes ineffective. The present invention discloses a method to increase the immunogenicity and therefore effectiveness of a recombinant bacterial vaccine vector, including a *Listeria* vaccine vector. The present invention further includes a method to increase the immunogenicity of an antigen in a bacterial vaccine vector, including a *Listeria* vaccine vector.

The data disclosed herein demonstrate, for the first time, that passaging a recombinant bacterial vaccine vector, including a *Listeria* vaccine vector, through an in vivo system a number of times results in, among other things, an increase in the immunogenicity of the antigen and/or fusion protein, and increases the induction of a $CD8^+$ T-cell response towards the antigen and/or fusion protein. That is, as disclosed herein, administering to an animal a bacterial vaccine vector that has been passaged repeatedly through an animal until a maximum bacterial virulence is achieved results in, inter alia, an increased induction of a $CD8^+$ cell-mediated immune response against antigens from both tumors and intracellular pathogens such as viruses and bacteria. Further, the data disclosed herein demonstrate that passaging a bacterial vaccine vector, such as a *Listeria* vaccine vector, increases the virulence of the bacterial vaccine vector, as measured by, inter alia, an increased bacterial load. Therefore, the data disclosed herein demonstrate that passaging a bacterial vaccine vector through an animal results in enhanced immunogenicity in both the bacterial vaccine vector and the antigens comprising the bacterial vaccine vector when compared to a bacterial vaccine vector that has not been passaged through an animal. The skilled artisan will appreciate that the enhanced immunogenicity of an antigen and/or fusion protein and an increased $CD8^+$ T-cell response to antigen and/or fusion protein is beneficial and useful for vaccine therapy in general, specifically to the prevention, treatment, and alleviation of tumors and the sequelae of intracellular pathogens.

The present invention comprises administering to a mammal a bacterial vaccine vector, including a *Listeria* vaccine vector comprising an antigen, preferably a heterologous antigen. Methods for constructing a *Listeria* vaccine vector comprising an antigen, heterologous antigen and/or fusion protein from a plasmid and methods for constructing a *Listeria* vaccine vector comprising an antigen or a heterologous antigen expressed from the Listerial chromosome are well known in the art, and are described in, for example, Portnoy and Paterson (U.S. Pat. No. 5,830,702) and Paterson (U.S. Pat. No. 6,051,237), which are hereby incorporated by reference in their entirety herein.

The antigen or heterologous antigen of the present invention is preferably an antigen derived from a tumor or an infectious organism, including, but not limited to a fungal pathogen, bacteria, a parasite, a helminth, a virus, and the like. An antigen or heterologous antigen of the present invention includes, but is not limited to, a tetanus toxoid, a hemagglutinin molecule from an influenza virus, a nucleoprotein molecule from an influenza virus, a diphtheria toxoid, a HIV gp120 molecule, or portions thereof, a HIV gag protein, an IgA protease, an insulin peptide B, a *Spongospora subterranea* antigen, a vibriose antigen, a *Salmonella* antigen, a pneumococcus antigen, a respiratory syncytial virus antigen, a *Haemophilus influenza* outer membrane protein, a *Streptococcus pneumoniae* antigen, a *Helicobacter pylori* urease, a *Neisseria meningitidis* pilin, a *N. gonorrhoeae* pilin, a melanoma-associated antigen (TRP-2, MAGE-1, MAGE-3, gp-100, tyrosinase, MART-1, HSP-70, beta-HCG), a human papilloma virus antigen, including E1, E2, E6 and E7 from type HPV-16, -18, -31, -33, -35 or -45 human papilloma virus, a CEA tumor antigen, a ras protein, mutated or otherwise, a p53 protein, mutated or otherwise, Muc1, pSA, an antigen well known in the art from the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, an immunogen and/or antigen from Addison's disease, an allergen, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as a kidney, heart, pancreas, lung, bone, and liver transplant, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, a rheumatic disease, systemic lupus erthematosus, rheumatoid arthritis, seronegative spondylarthritides, rhinitis, Sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, a malarial circumsporozite protein, a microbial antigen, a viral antigen, an autoantigen, and lesteriosis.

A tumor antigen contemplated in the present invention includes, but is not limited to, a MAGE antigen (Melanoma-Associated Antigen E), including MAGE 1 (e.g., GenBank Accession No. M77481), MAGE 2 (e.g., GenBank Accession No. U03735), MAGE 3, MAGE 4, etc.; a tyrosinase; a mutant ras; a mutant p53 (e.g., GenBank Accession No. X54156 and AA494311); and p97 melanoma antigen (e.g., GenBank Accession No. M12154). Other tumor-specific antigens encompassed in the present invention include the Ras peptide and p53 peptide associated with advanced cancers, the HPV 16/18 and E6/E7 antigens associated with cervical cancers, the bcr/abl leukemia antigen, the MZ2-E melanoma antigen, the MVC-1 breast and pancreatic carcinoma antigen, MUC1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. A tumor antigen of the present invention further includes an NY-ESO-1 antigen (GenBank Acc. No. U87459) and Her-2/neu (GenBank Acc. Nos. M16789.1, M16790.1, M16791.1, M16792.1). Thus, the present invention can be used as immunotherapeutics for cancers including, but not limited to, cervical, breast, colorectal, prostate, lung cancers, and for melanomas.

The present invention further includes, but is not limited to the antigens from the following infectious diseases, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and AIDS (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), arnoebiasis, filariasis (e.g., GenBank Accession No. J03266), borreliosis, and trichinosis.

The passaging process can be performed as follows. The bacterial vaccine vector is grown in liquid media using materials and reagents well known in the art for growing and propagating bacterial species. Further, one of skill in the art will readily understand that bacteria are grown from a single clone in order to insure that a homogenous population of bacteria are used in the methods disclosed herein. A single clone is grown in an appropriate liquid medium until an appropriate optical density is attained. Methods for measuring the optical density of a bacterial population are well known in the art and include spectroscopy, turbidity analysis, and the like. The media may comprise a selection media if necessary, in order to facilitate the retention of the heterologous antigen.

The prudent skilled artisan will know that in order to guarantee the expression of a heterologous antigen and/or fusion protein, such expression should be monitored after each passage or growth cycle. Measurement of the expression of a protein from a bacterial population is a skill well known in the art, and the present invention contemplates methods such as immunoblotting, Western blotting, ELISA, and other such assays for protein expression well known in the art. Bacterial clones that retain the ability to express such antigens and/or fusion proteins are then selected for the next round of bacterial replication. The skilled artisan, when equipped with the methods disclosed herein will therefore be able to select a bacterial vaccine vector that stably and predictably expresses a heterologous antigen and/or fusion protein.

After selection of a bacterial vaccine vector stably and predictably expressing a heterologous antigen and/or fusion protein, the bacterial vaccine vector is administered to a mammal. The present invention contemplates the use of mammals such as mice, rabbits, guinea pigs, hamsters, gerbils, rats, and the like. Such mammals are well known in the art and are available to the skilled artisan through a variety of wholesalers, distributors, and laboratories, for example, Jackson Laboratories (Bar Harbor, Me.). As a non-limiting example, if mice are to be used in the methods of the present invention, such mice should be from about six weeks to about eight weeks old, however other ages are suitable and can be selected by the skilled artisan. One of ordinary skill in the art will readily recognize the age ranges and physical appearance of a mammal that is amendable to the methods of the present invention. Such animals can be maintained in a standard animal facility environment, or in pathogen-free conditions well known in the art.

The titer of bacterial vaccine vector to be administered to a mammal for passaging may be determined by various methods including turbidity assays, optical density readings and dilution of a cellular population followed by plating and counting methods. For example, after a single colony expressing a heterologous antigen and/or fusion protein is selected, it may be grown in liquid media, and then plated on appropriate solid media at various dilutions in order to determine the viability and number of bacteria in a pre-determined volume. Such techniques, and others, are well known in the art.

The bacterial vaccine vector, after determination of titer, is then administered to a suitable animal, described elsewhere herein. As is well known in the art, a suitable method for the administration of bacteria to a mammal comprises parenteral or oral administration of the bacteria. Parenteral administration includes, intramuscular, subcutaneous, intradermal and intravenous administration. Preferably, the administration comprises intravenous administration into a suitable animal.

The titer of the inoculum will vary depending on the size, health, and susceptibility of the animal, the virulence of the bacterial vaccine vector, and with other considerations well known in the art. As an example, from about $1 \times 10^3$ to about $1 \times 10^6$, more preferably about $2 \times 10^5$ to about $9 \times 10^5$, even more preferably about $3 \times 10^5$ to about $8 \times 10^5$, yet still more preferably about $4 \times 10^5$ to about $6 \times 10^5$, and even more preferably about $5 \times 10^5$ bacteria will be inoculated intravenously into an appropriate animal. Alternatively, a similar number of a bacterial vaccine vector can be administered orally. The same number of bacteria are administered in each subsequent passage. As an example, if about $5 \times 10^5$ bacteria are administered to an animal in the first passage, about $5\times10^5$ bacteria are administered to an animal in each subsequent passage.

After a period of time, the bacterial vaccine vector is harvested from the animal for further passage. The bacterial vaccine vector may be harvested from about 1 to about 9 days after inoculation, preferably about 2 to about 7 days after inoculation, more preferably about 3 to about 5 days after inoculation, even more preferably about 3 to about 4 days after inoculation, most preferably about 3 days after inoculation. However, as demonstrated by the data disclosed elsewhere herein, the time of harvesting will depend on the virulence of the bacterial vaccine vector and the antigen expressed therefrom.

The bacterial vaccine vector is harvested from the spleen, liver or other infected organ or tissue of the suitable inoculated animal. A suitable organ or tissue includes, but is not limited to an organ or tissue which is capable of being infected by a bacterial vaccine vector and then the bacterial vaccine vector can be harvested. Such an organ or tissue includes the brain, liver, spleen, heart, spinal cord, spinal fluid, peripheral nerve, skin, pancreas, lymph node, eye, kidney, macrophage, epithelial cell, fibroblast, and the like. Harvesting spleens, for example, is well known in the art, and is described in detail in, for example, Harlow et al. (1988, Antibodies: A Laboratory Manual, Cold Spring Harbor, N.Y.). Briefly, the spleen is harvested, homogenized and serial dilutions are grown in the appropriate nutrient broth overnight and plated for colony counting as described elsewhere herein. The passaging process described herein is repeated as desired until the maximum acterial virulence, and thus the greatest immunogenicity, is achieved.

The skilled artisan, when armed with the present invention and the data disclosed herein, will recognize that the number of passages in an animal is not limited to a fixed number, but rather is determined by the bacterial load harvested from the animal. Thus, an animal is inoculated with a bacterial vaccine vector and the bacterial vaccine vector is harvested and the number of bacteria recovered is determined according to methods well known in the art and described elsewhere herein. This process is repeated and the number of bacteria recovered from passage 0 (the first passage) is compared to number of bacteria recovered from passage 1 (the second passage). The number of bacteria from passage 1 may be higher, lower, or the same as the number of bacteria from passage 0, but, as demonstrated by the data disclosed herein, the number of bacteria harvested from passage 1 will be higher than the number of bacteria harvested from passage 0. The process is repeated again, and the number of bacteria from passage 2 is compared to the number of bacteria harvested from passage 1. As demonstrated by the data disclosed elsewhere herein, the number of bacteria from passage 2 will be higher than the number of bacteria from passage 1. The process is again repeated and the number of bacteria from passage 3 is compared to the number of bacteria from passage 2. If the number of bacteria from passage 3 is higher than the number of bacteria from passage 2, the passaging process is repeated again until the maximum bacterial load is achieved. If the number of bacteria harvested from passage 3 is lower than the number of bacteria harvested from passage 2, passage 2 comprises the maximum bacterial virulence, and thus, as demonstrated by the data disclosed herein, the bacteria recovered from the maximum bacterial load have greatly enhanced immunogenicity when compared to unpassaged bacteria. Further, as disclosed by the data herein, the antigen, including an endogenous antigen, a heterologous antigen, and a tumor antigen expressed from the bacterial vaccine vector, will have enhanced immunogenicity when compared to an antigen expressed from unpassaged bacteria. Thus, the maximum bacterial virulence is determined when the number of bacteria harvested after a passage is greater than the number of bacteria harvested from the previous passage, and is also greater than the number of bacteria harvested from the subsequent passage. Therefore, bacterial vaccine vectors from the maximum bacterial load are administered to an animal, including humans, to elicit immunity to an antigen expressed by the bacterial vaccine vector, and as demonstrated by the data disclosed herein, administration of such bacterial vaccine vectors to an animal results in, inter alia, enhanced immunogenicity and a stronger $CD8^+$ response to an antigen. That is, as demonstrated by the data disclosed herein, administering a bacterial vaccine vector derived from the maximum bacterial load after serial passages to an animal results in enhanced virulence and thus enhanced immunogenicity. Moreover, as demonstrated by the data disclosed herein, administering a bacterial vaccine vector derived from the maximum bacterial load after passaging through an animal results in enhanced immunogenicity of the antigen in the bacterial vaccine vector. Passaging, among other things, therefore provides a method for enhancing the immunogenicity of the bacterial vaccine vector.

The present invention further comprises a composition comprising a bacterial vaccine vector, such as a *Listeria* vaccine vector, produced by the methods disclosed elsewhere herein. The bacterial vaccine vector is administered to an animal, passaged through the animal, harvested from the animal, and thereby, as demonstrated by the data disclosed herein, has an enhanced immunogenicity.

The bacterial vaccine vector comprises an antigen, preferably a heterologous antigen, and even more preferably, a tumor antigen. Such antigens are detailed elsewhere herein, and include, but are not limited to a tumor antigen, such as an antigen from prostate cancer, an antigen from breast cancer, an antigen from leukemia, an antigen from melanoma, and an antigen from cervical cancer, and the like.

The invention also encompasses the use of pharmaceutical compositions of an appropriate bacterial vaccine vector, including a *Listeria* vaccine vector, to practice the methods of the invention, the compositions comprising an appropriate bacterial vaccine vector and a pharmaceutically-acceptable carrier.

As used herein, the term "pharmaceutically-acceptable carrier" means a chemical composition with which an appropriate bacterial vaccine vector may be combined and which, following the combination, can be used to administer the appropriate bacterial vaccine vector to a mammal.

Pharmaceutical compositions that are useful in the methods of the invention may be administered systemically in oral solid formulations, ophthalmic, suppository, aerosol, topical or other similar formulations. In addition to the appropriate bacterial vaccine vector, such pharmaceutical compositions may contain pharmaceutically-acceptable carriers and other ingredients known to enhance and facilitate bacterial vaccine vector administration. Other possible formulations, such as nanoparticles, liposomes, resealed erythrocytes, and immunologically based systems may also be used to administer an appropriate bacterial vaccine vector according to the methods of the invention.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, cutaneous, intraperitoneal, transdermal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 µg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising a bacterial vaccine vector, such as a *Listeria* vaccine vector with enhanced immunogenicity, of the invention and an instructional material which describes adventitially administering the composition to a cell or a tissue of a mammal or a whole mammal. In another embodiment, this kit comprises a (preferably sterile) solvent suitable for dissolving or suspending the composition of the invention prior to administering the compound to the mammal.

The kit comprises a bacterial vaccine vector, such as a *Listeria* vaccine vector with enhanced immunogenicity. The immunogenicity of the bacterial vaccine vector is enhanced using the methods of the present invention described elsewhere herein. The kit further comprises an instructional material and an applicator.

The bacterial vaccine vector can be incorporated into the kit in various forms, including as a lyophilized powder or solid with a solution or fluid for reconstitution, as a frozen culture of bacterial vaccine vector, as a suspension of bacteria in a pharmaceutically acceptable carrier, as solid agar comprising a bacterial vaccine vector, and the like. The kit further comprises an applicator, an instructional material and a pharmaceutically-acceptable carrier.

As used herein, an "instructional material" includes a publication, a recording, a diagram, or any other medium of expression which can be used to communicate the usefulness of the present invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the present invention or be shipped together with a container which contains the bacterial vaccine vector. Alternatively, the instructional material may be shipped separately from the container with the intention that the instructional material and the compound be used cooperatively by the recipient. These instructions simply embody the examples provided herein.

An applicator is a device or composition for administration of a bacterial vaccine vector. Applicators include, but are not limited to syringes, pipettes, and other materials necessary for the administration of a bacterial vaccine vector, including a *Listeria* vaccine vector by routes including parenteral administration, oral administration, intramuscular administration, intravenous administration, and other methods of administration disclosed elsewhere herein and well known in the art. The bacterial vaccine vector is provided in an appropriate amount as set forth elsewhere herein. Further, the route of administration and the frequency of administration are as previously set forth elsewhere herein.

The invention is now described with reference to the following examples. These Examples are provided for the purpose of illustration only, and the invention should in no way be construed as being limited to these Examples, but rather should be construed to encompass any and all variations which become evident as a result of the teaching provided herein.

Example 1

Passaging of *Listeria* Vaccine Vectors Through Mice Elicits an Increased Immune Response to Both Heterologous and Endogenous Antigens

*Listeria* vaccine vectors have been shown to be useful for the induction of a protective immune response, especially an immune response to tumor antigens and intracellular pathogens such as viruses, intracellular bacteria, and parasites.

To create *Listeria* vaccine vectors, the skilled artisan must manipulate and grow *Listeria* in an in vitro environment. While such an environment facilitates cloning and other molecular biology techniques, there is no pressure on the *Listeria* vaccine vector to express virulence factors that may lead to an overly attenuated phenotype incapable of eliciting an immune response in the vaccinee. While an attenuated phenotype is desired, if a *Listeria* vaccine vector is unable to survive for any amount of time in the intracellular environment, there is no possibility of generating any cellular immunity to a heterologous antigen and/or fusion protein.

The data disclosed herein demonstrate an efficient and effective method for increasing the immunogenicity of a *Listeria* vaccine vector, especially a cellular immune response useful in preventing and treating tumors and intracellular pathogens.

Bacterial Strains

*L. monocytogenes* strain 10403S, serotype 1 (ATCC, Manassas, Va.) was the wild type organism used in these studies and the parental strain of the constructs described below. Strain 10403S has an $LD_{50}$ of approximately $5 \times 10^4$ CFU when injected intraperitoneally into BALB/c mice. Lm-Gag refers to a recombinant strain of *L. monocytogenes* comprising a copy of the HIV-1 strain HXB (subtype B laboratory strain with a syncitia forming phenotype) gag gene stably integrated into the listerial chromosome using a modified shuttle vector pKSV7 as previously described (Mata et al, 2001, Vaccine 19:1435-1445). Gag protein is expressed and secreted by *L. monocytogenes* as determined by Western blot. Lm-E7 refers to a recombinant strain of *L. monocytogenes* which carries a copy of the human papilloma virus (HPV) E7 gene in the listerial chromosome. Lm-E7 was constructed similarly to Lm-Gag with some modifications. Lm-LLO-E7 is constructed as a hly-E7 fusion gene in an episomal expression system. The construction of both E7 expressing recombinant strains is described in detail in, for example, Gunn et al (2001, J. Immunol. 167:6471-6479). All strains were grown in brain-heart infusion (BHI) broth or agar plates (Difco Labs, Detroit, Mich.).

Bacterial Culture

Preparation of bacterial pools for passaging proceeded substantially as described herein. Bacteria from a single clone expressing the passenger antigen and/or fusion protein were selected and cultured in BHI broth overnight. Aliquots of this culture were frozen at −70° C. with no additives. From this stock, cultures were grown to 0.1-0.2 O.D. at 600 nm, and aliquots were again frozen at −70° C. with no additives. To prepare cloned bacterial pools, the above procedure was used, but after each passage a number of bacterial clones were selected and checked for expression of the target antigen, as described herein. Clones in which expression of the foreign antigen was confirmed were used for the next passage.

Passage of Bacteria in Mice

Female BALB/c (H-2d) mice were purchased from Jackson Laboratories (Bar Harbor, Me.). All mice were maintained in a pathogen-free microisolator environment. Mice used in this study were about 6-8 weeks old. The titer of viable bacteria in an aliquot of stock culture, stored frozen at −70° C., was determined by plating on BHI agar plates on thawing and prior to use. In all $5 \times 10^5$ bacteria were injected intravenously into BALB/c mice. After 3 days, the spleen was harvested, homogenized, and serial dilutions of the spleen homogenate were incubated in BHI broth overnight and plated on BHI agar plates. For further passage, aliquots were again grown to 0.1-0.2 O.D., frozen at −70° C., and the bacterial titer was again determined by serial dilution. After the initial passage (passage 0), this sequence was repeated for a total of four times.

Intracellular Cytokine Stain for IFN-Gamma

Lymphocytes were cultured for 5 hours in complete RPMI-10 medium supplemented with 50 U/ml human recombinant IL-2 and 1 microliter/ml Brefeldin A (Golgistop™; PharMingen, San Diego, Calif.) in the presence or absence of either the cytotoxic T-cell (CTL) epitope for HIV-GAG (AMQMLKETI (SEQ ID NO:1)), *Listeria* LLO (GYKDGNEYI (SEQ ID NO:2)) or the HPV virus gene E7 (RAHYNIVTF (SEQ ID NO:3). The peptides were used at a concentration of 1 micromole. The cells were first surface-stained, then washed and subjected to intracellular cytokine stain using the Cytofix/Cytoperm kit in accordance with the manufacturer's recommendations (PharMingen, San Diego, Calif.). For intracellular IFN-gamma stain, FITC-conjugated rat anti mouse IFN-gamma monoclonal antibody (clone XMG 1.2) and its isotype control Ab (rat IgG1; both from PharMingen, San Diego, Calif.) was used. In all 106 cells were stained in PBS containing 1% Bovine Serum Albumin and 0.02% sodium azide (FACS Buffer) for 30 minutes at 4° C. followed by three washes in FACS buffer. Sample data were acquired on either a FACScan™ flowcytometer or FACSCalibur™ instrument (Becton Dickinson, San Jose, Calif.). Three-color flow cytometry for CD8 (PERCP conjugated, rat anti mouse, clone 53-6.7 Pharmingen, San Diego, Calif.), CD62L (APC conjugated, rat anti mouse, clone MEL-14) and intracellular IFN-gamma was performed using a FACSCalibur™ flow cytometer and data were further analyzed with CELLQuest software (Becton Dickinson, Mountain View, Calif.). Cells were gated on CD8 high and CD62L$^{low}$ before they were analyzed for CD8$^+$ and intracellular IFN-gamma staining.

Results

The results of the experiments presented in this Example are now described.

Passaging Recombinant *L. monocytogenes* in Mice Increases its Virulence

Figure 1B:
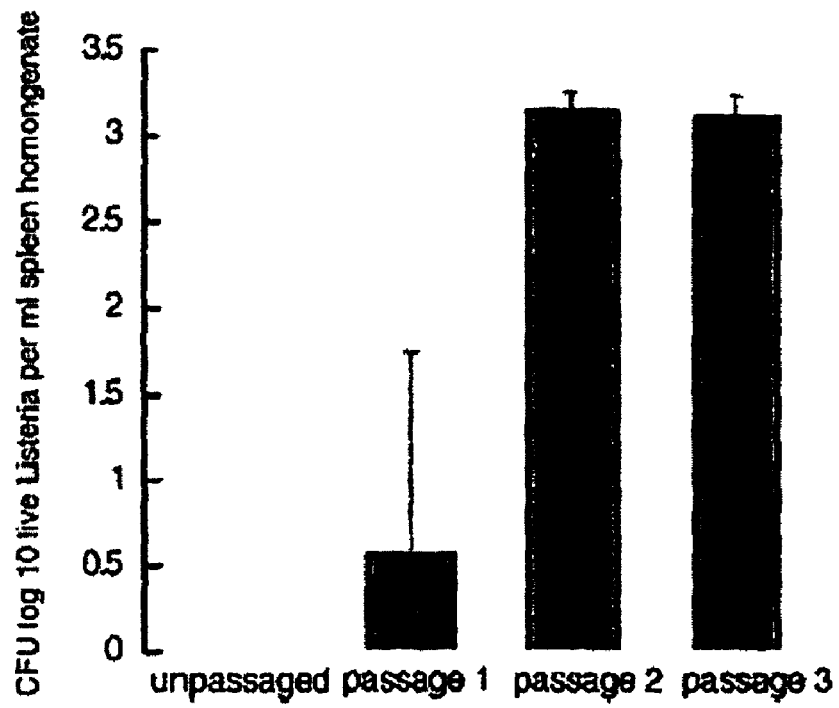
Figure 2:
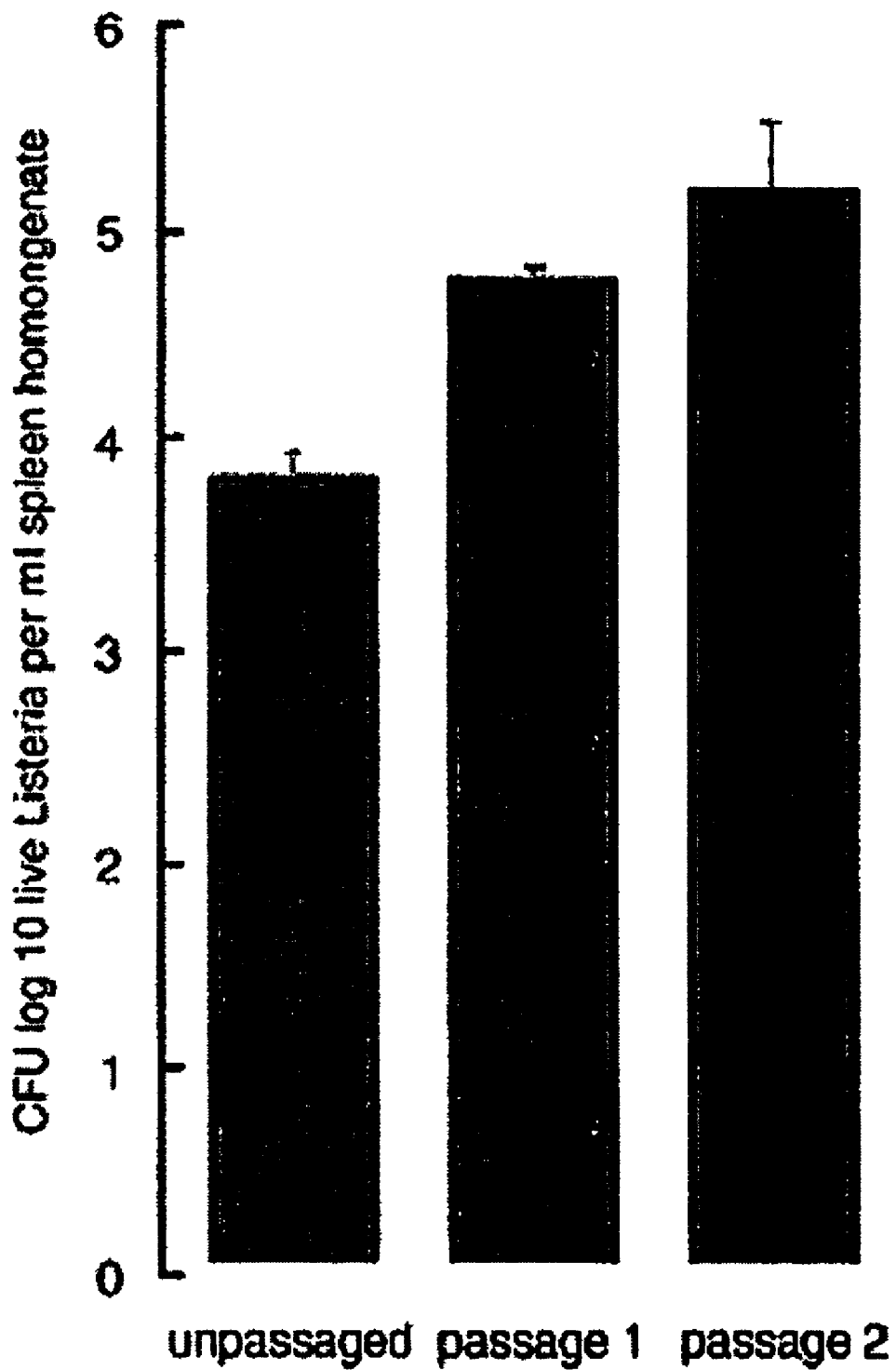
FIG. 2 is a graph depicting the effects of passaging on bacterial load (virulence) of cloned recombinant Lm-E7 in the spleen. The average CFU of live bacteria per milliliter of spleen homogenate from four mice is depicted.
Figure 3A:
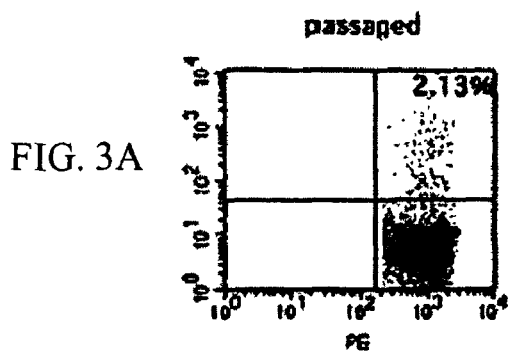
FIGS. 3A through 3J, depicts the induction of antigen-specific $CD8^+$ T-cells for HIV-Gag and LLO after administration of passaged Lm-Gag versus unpassaged Lm-Gag.
Figure 3B:
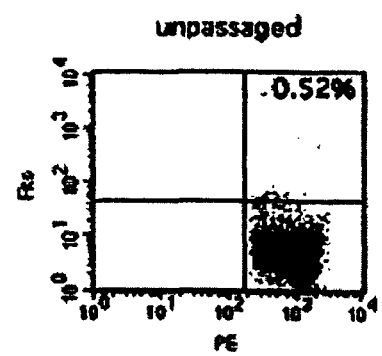
Figure 3C:
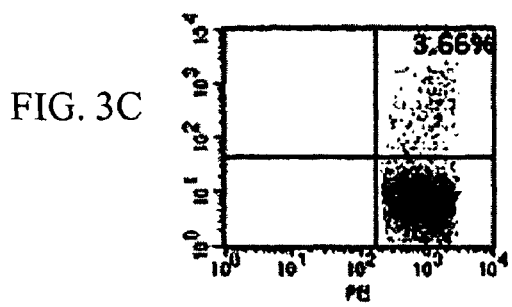
Figure 3D:
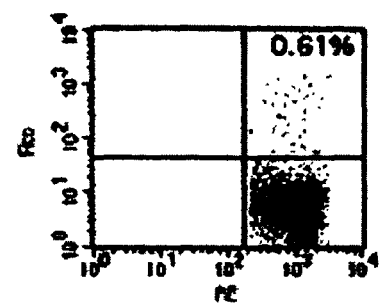
Figure 3E:
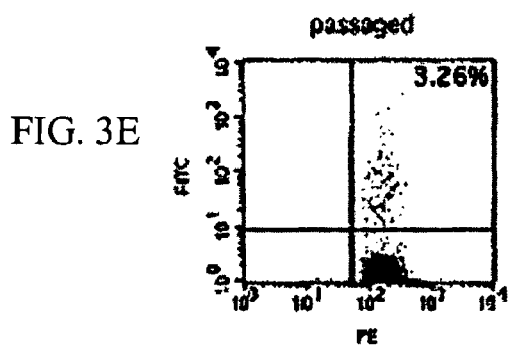
Figure 3F:
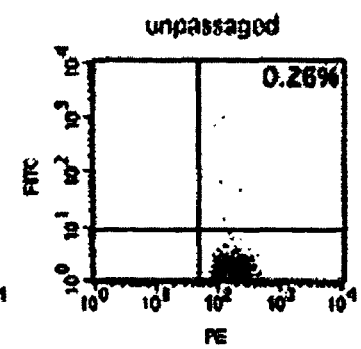
Figure 3G:
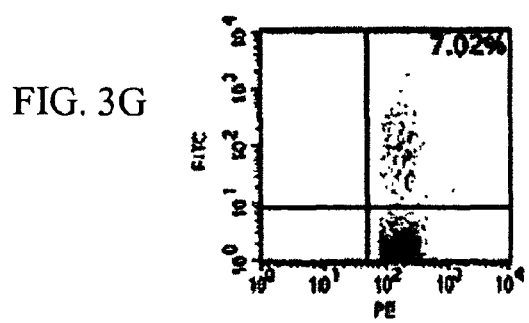
Figure 3H:
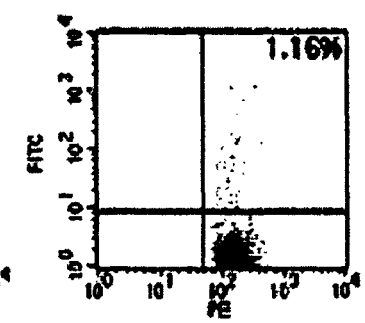
Figure 3I:
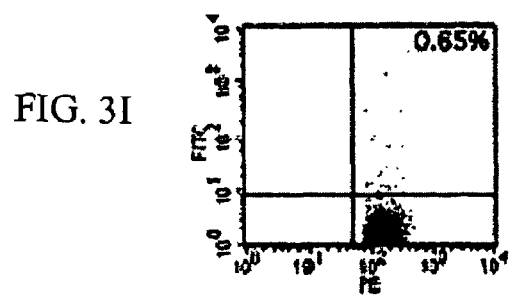
Figure 3J:
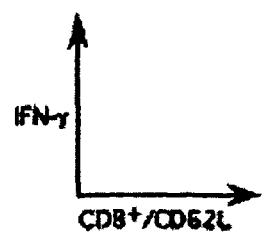

Three different constructs were used to determine the impact of passaging on recombinant *Listeria* vaccine vectors. Two of these constructs carry a genomic insertion of the passenger antigen: the first comprises the HIV gag gene (Lm-Gag), and the second comprises the HPV E7 gene (Lm-E7). The third (Lm-LLO-E7) comprises a plasmid with the fusion gene for the passenger antigen (HPV E7) fused with a truncated version of LLO and a gene encoding prfA, the positive regulatory factor that controls *Listeria* virulence factors. This plasmid was used to complement a prfA negative mutant so that in a live host, selection pressures would favor conservation of the plasmid, because without it the bacterium is avirulent. All three constructs had been propagated extensively in vitro for many bacterial generations. As demonstrated by the data disclosed herein, bacterial virulence, as measured by numbers of surviving bacteria in the spleen, increases with each of the first two passages. With Lm-Gag and Lm-LLO-E7, virulence increased with each passage up to passage 2 (FIG. 1). The plasmid-containing construct, Lm-LLO-E7, demonstrated the most dramatic increase in virulence. In the case of the Lm-LLO-E7 construct, the initial immunizing dose of bacteria had to be increased to 10 bacteria and the spleen had to be harvested on day 2 in order to recover bacteria, whereas an initial dose of $10^5$ bacteria for Lm-Gag was harvested on day 3. After the initial passage, the standard dosage was sufficient to allow harvesting on day 3. In Lm-E7, cloning of a bacteria expressing the passenger antigen produced by passage 1 and a repeated passaging procedure demonstrated that the virulence of the intact Lm-E7 increased by about 1.5 logs over unpassaged bacteria (FIG. 2). Therefore, the data disclosed herein demonstrate that even the initial passage increased the virulence of the bacteria sufficiently to facilitate reproduction despite the rigors of the host environment.

Passaging Increases the Ability of *L. monocytogenes* to Induce CD8$^+$ T-Cells

While the data disclosed thus far demonstrate that passaging a *Listeria* vaccine vector through a mammal increases both the virulence and ability to propagate in vivo, it was also necessary to determine whether passaging effects the induction of antigen-specific CD8$^+$ T-cells. Intracellular cytokine staining with immunodominant peptides specific for MHC-class I using HIV-Gag peptide AMQMLKETI (SEQ ID NO:1) and LLO 91-99 (GYKDGNEYI) (SEQ ID NO:2) were used to this end. A dose of $10^3$ CFU passaged bacteria (Lm-Gag) were injected into mice, resulting in a good induction of HIV-Gag-specific CD8$^+$ T-cells. However, the same dose of non-passaged Lm-Gag induced no detectable level of HIV-Gag-specific CD8$^+$ T-cells. In order to investigate whether a higher dose of unpassaged bacteria would compensate for their relative avirulence, a 100-fold higher dose of unpassaged bacteria were administered, but still did not yield any detectable induction, while the same dose increase with passaged bacteria increased the number of HIV-Gag-specific T-cells by 50% (FIG. 3).

To analyze whether the lack of induction of CD8$^+$ T-cells with unpassaged bacteria is linked to properties of the passenger antigen, the induction of listeriolysin-specific CD8$^+$ T-cells was investigated. LLO elicits a similar pattern of immune response: a low dose of passaged bacteria elicited a good response, while a low dose of unpassaged bacteria elicited no detectable response (a high dose elicited a moderate response). Thus, the failure to induce antigen-specific CD8$^+$ T-cells in animals inoculated unpassaged cells is not restricted to the passenger antigen but also extends to LLO, an endogenous antigen of *Listeria*.

The disclosures of each and every patent, patent application, and publication cited herein are incorporated herein by reference in their entirety.

While the invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed:

1. A method of enhancing the immunogenicity of a bacterial vaccine vector expressing a heterologous antigen, the method comprising the steps of: a) administering to a non-human animal the bacterial vaccine vector; b) passaging the bacterial vaccine vector through the animal; c) harvesting the bacterial vaccine vector from a normal organ or normal tissue in the non-human animal; and d) repeating step a), step b), and step c) with the harvested bacterial vaccine vector until a maximum bacterial load for said vector in said organ or tissue is reached; wherein said maximum bacterial load is reached by the $2^{nd}$ passage, wherein said bacterial vector from said maximum bacterial load has reached the maximum bacterial virulence, wherein administering said bacterial vector derived from said maximum bacterial load to a human subject after passaging through said non-human animal results in enhanced immunogenicity of said heterologous antigen in said bacterial vaccine vector, and wherein the bacterial vaccine vector is a Listeria vaccine vector.

2. The method of claim 1, wherein the organ is a spleen or liver.

3. The method of claim 1, wherein the antigen is a tumor antigen.

4. The method of claim 1, wherein the animal is a mammal.

5. The method of claim 4, wherein the mammal is a mouse.

6. The method of claim 1, further comprising the step of administering the bacterial vaccine vector to a human via oral or parenteral administration following the step of harvesting the vector after achieving a maximum bacterial load in said non-human animal.

7. A method of enhancing the immunogenicity of an antigen expressed from a bacterial vaccine vector, the method comprising the steps of: a) administering to a non-human animal the bacterial vaccine vector; b) passaging the bacterial vaccine vector through the non-human animal; c) harvesting the bacterial vaccine vector from a normal organ or normal tissue in the non-human animal; and d) repeating step a), step b), and step c) with the harvested bacterial vaccine vector until a maximum bacterial load for said vector in said organ or tissue is reached; wherein said maximum bacterial load is reached by the $2^{nd}$ passage, wherein said bacterial vector from said maximum bacterial load has reached the maximum bacterial virulence, wherein administering said bacterial vector derived from said maximum bacterial load to a human subject after passaging through said non-human animal results in enhanced immunogenicity of said heterologous antigen in said bacterial vaccine vector, and wherein the bacterial vaccine vector is a *Listeria* vaccine vector.

8. The method of claim 7, wherein the organ is a spleen or liver.

9. The method of claim 7, wherein the antigen is a tumor antigen.

10. The method of claim 7, wherein the animal is a mammal.

11. The method of claim 10, wherein the mammal is a mouse.

12. The method of claim 7, further comprising the step of administering the bacterial vaccine vector to a human via oral or parenteral administration following the step of harvesting the vector after achieving a maximum bacterial load in said non-human animal.

* * * * *